United States Patent
Park et al.

(10) Patent No.: US 10,251,955 B1
(45) Date of Patent: *Apr. 9, 2019

(54) HEPARIN-MIMICKING SULFONATED REVERSE THERMAL GEL FOR THE DELIVERY OF HEPARIN-BINDING THERAPEUTIC PROTEINS

(71) Applicant: The Regents of the University of Colorado, A Body Corporate, Denver, CO (US)

(72) Inventors: Daewon Park, Englewood, CO (US); Brisa Pena-Castellanos, Aurora, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/645,384

(22) Filed: Jul. 10, 2017

Related U.S. Application Data

(63) Continuation of application No. 14/880,685, filed on Oct. 12, 2015, now Pat. No. 9,700,628.

(60) Provisional application No. 62/062,545, filed on Oct. 10, 2014.

(51) Int. Cl.
 *A61K 47/34* (2017.01)
 *A61K 9/00* (2006.01)
 *A61K 38/38* (2006.01)

(52) U.S. Cl.
 CPC ............ *A61K 47/34* (2013.01); *A61K 9/0024* (2013.01); *A61K 38/385* (2013.01)

(58) Field of Classification Search
 None
 See application file for complete search history.

(56) References Cited

U.S. PATENT DOCUMENTS 9,700,628 B1 * 7/2017 Park ........................ A61K 47/34
2016/0051469 A1 * 2/2016 Park ...................... A61K 9/0024
424/451

OTHER PUBLICATIONS

Nguyen et al. A heparin-mimicking polymer conjugate stabilizes fibroblast growth factor, Nature Chemistry, Feb. 17, 2013. (Year: 2013).*

Kanabar, V et al. "Heparin and Structurally Related Polymers Attenuate Eotaxin-1 (CCL11) Release from Human Airway Smooth Muscle." British Journal of Pharmacology 154.4 (2008): 833-842. PMC. Web. Jan. 13, 2016.

(Continued)

*Primary Examiner* — Robert A Wax
*Assistant Examiner* — Melissa S Mercier
(74) *Attorney, Agent, or Firm* — Michael M. McGaw; Smith & Hopen, P.A.

(57) ABSTRACT

A heparin-mimicking sulfonated reverse thermal gel (SRTG) as a heparin-binding therapeutic protein delivery system. This system is designed to turn from low viscous liquid to a physical gel by exposure to body temperature alone. This allows direct deployment through a small gauge needle or catheter at target area with minimal surgical intervention. A unique aspect of this system is that it possesses a net negative charge due to the presence of sulfonate groups. This allows the SRTG to mimic heparin function, binding and preserving the bioactivity of positively charged therapeutic proteins, providing localized and sustained release of such proteins.

20 Claims, 12 Drawing Sheets

(56) References Cited

OTHER PUBLICATIONS

Nguyen TH, et al., A heparin-mimicking polymer conjugate stabilizes basic fibroblast growth factor. Nature Chemistry 2013;5(3):221-227.

Guan, R., Sun, X. L., Hou, S. J., Wu, P. Y. & Chaikof, E. L. A glycopolymer chaperone for fibroblast growth factor-2. Bioconj. Chem. 15, 145-151 (2004).

Liekens, S. et al. Modulation of fibroblast growth factor-2 receptor binding, signaling, and mitogenic activity by heparin-mimicking polysulfonated compounds. Mol. Pharmacol. 56, 204-213 (1999).

Sangaj N, et al., Heparin Mimicking Polymer Promotes Myogenic Differentiation of Muscle Progenitor Cells. Biomacromolecules 2010;11(12):3294-3300.

Chu HH, et al., A [polycation:heparin] complex releases growth factors with enhanced bioactivity: Journal of Controlled Release 2011;150(2):157-163.

Park, Daewon, Wei Wu, and Yadong Wang. "A Functionalizable Reverse Thermal Gel Based on a polyurethane/PEG Block Copolymer." Biomaterials 32.3 (2011): 777-786. PMC. Web. Jan. 13, 2016.

Supino R. MTT assays. Methods Mol. Biol 1995;43:137-149.

Meerloo J, et al., Cell Sensitivity Assays: The MTT Assay. Methods Mol. Biol. 2011;731:237-245.

Moradhaseli S, et al., Cytotoxicity of ICD-85 NPs on Human Cervical Carcinoma HeLa Cells through Caspase-8 Mediated Pathway, Iran. J. Pharm. Res. 2013;12:155-163.

Yun.D, et al., A Biomimetic Reverse Thermal Gel for 3-Dimensional Neural Tissue Engineering. Austin J Biomed Eng. 2014;1(4): 1019.

Sundback CA, Shyu JY, Wang Y, et al. Biocompatibility analysis of poly(glycerol sebacate) as a nerve guide material. Biomaterials. 2005;26(27):5454-5464.

Greenfield, Norma J. "Using Circular Dichroism Spectra to Estimate Protein Secondary Structure." Nature protocols 1.6 (2006): 2876-2890. PMC. Web. Jan. 13, 2016.

Nelson DM, Ma ZW, Leeson CE, Wagner WR. Extended and sequential delivery of protein from injectable thermoresponsive hydrogels. Journal of Biomedical Materials Research Part A. 2012;100A:776-785.

Xiao Q, et al., Systematically investigation of interactions between BSA and different charge-capped CdSe/ZnS quantum dots. Journal of Photochemistry and Photobiology A: Chemistry 2012;249(0):53-60.

* cited by examiner

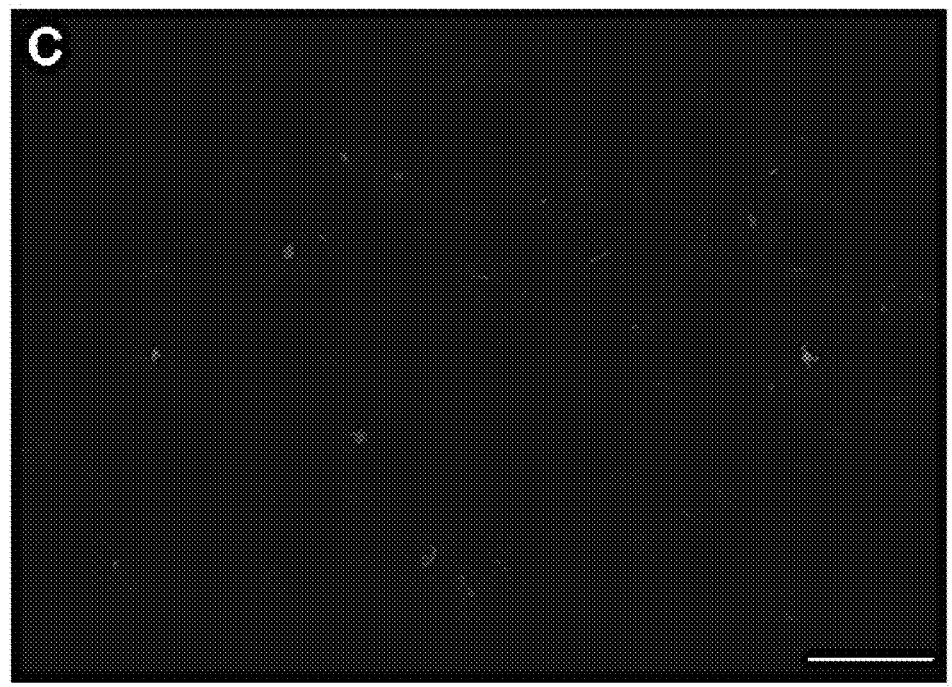
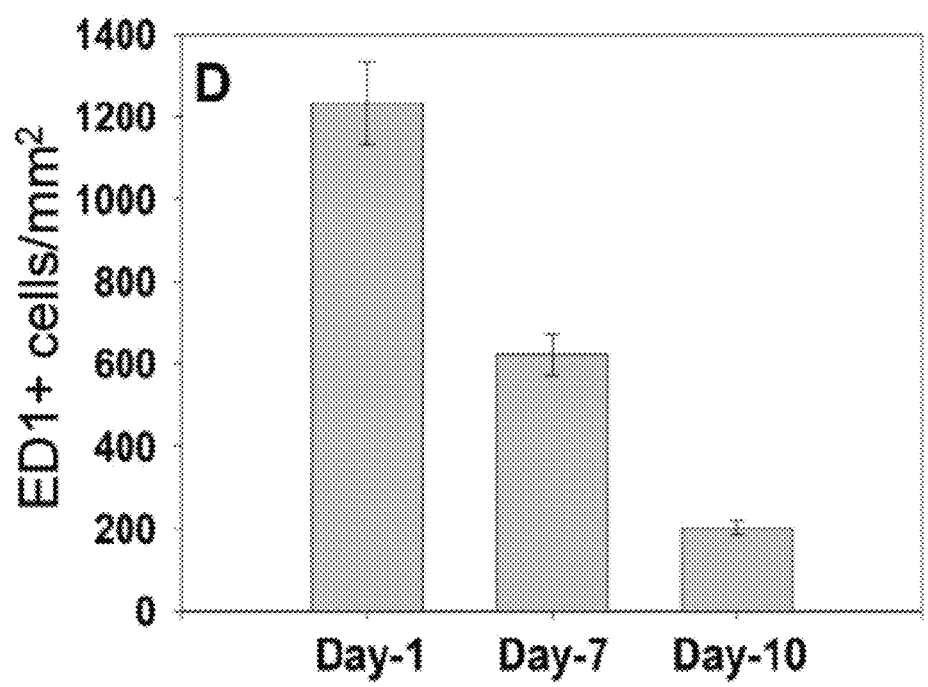
FIG. 8 - continued

HEPARIN-MIMICKING SULFONATED REVERSE THERMAL GEL FOR THE DELIVERY OF HEPARIN-BINDING THERAPEUTIC PROTEINS

CROSS-REFERENCE TO RELATED APPLICATIONS

This application is a continuation of U.S. application Ser. No. 14/880,685, filed Oct. 12, 2015, which claims the benefit of U.S. Provisional Application No. 62/062,545, filed Oct. 10, 2014.

STATEMENT OF GOVERNMENT INTEREST

This invention was made with government support under grant number HL124100 awarded by The National Institutes of Health. The government has certain rights in the invention.

BACKGROUND OF THE INVENTION

1. Field of Invention

This invention relates to reverse thermal gels. More specifically, this invention relates to heparin-mimicking sulfonated reverse thermal gel as a protein delivery system created by the sulfonation of a graft copolymer.

2. Brief Description of the Related Art

The development of smart, or stimuli-responsive, biomaterials is a major research focus in the field of tissue engineering and biomolecule delivery. Temperature-responsive reverse thermal gels (RTG) are a group of stimuli-responsive biomaterials that have gained much attention in recent investigations. At room temperature, RTG systems exist in a solution state (sol) with low viscosity that allows injection through a small gauge needle. Upon reaching body temperature, the RTG transitions from a low-viscosity sol to a semi-solid gel (sol-gel phase transition). This unique characteristic may be used to facilitate the delivery and subsequent release of sensitive therapeutic agents, such as cells, drugs or proteins, to a specific target site, avoiding side effects of invasive surgeries. In particular, an RTG can exist as a mobile viscous liquid at low temperatures, but RTGs become a more rigid semisolid gel at higher temperatures. By controlling the composition of the RTG, it is possible to use these polymers to design a formulation that is liquid at room temperature, but gels once injected. The RTG can then function as a depot of a drug at the injection site.

Heparin is a naturally sulfated biopolymer with an intrinsic negative charge. Heparin stores, protects and stabilizes positively charged heparin-binding proteins in the extracellular matrix (ECM) and plays an important role in the regulation of cellular proliferation and differentiation. Due to heparin's ability to associate with positively charged heparin-binding proteins, a vast number of heparin-conjugated protein delivery systems have been investigated. However, heparin has major limitations. It is difficult to modify, susceptible to desulfation, and presents batch-to-batch variability in structure and biocompatibility. It also has significant undesirable activity in other non-target biological pathways [Kanabar V, et al., British Journal of Pharmacology 2008; 154(4):833-842]. Moreover, it may inhibit the normal growth of certain cells, such as human umbilical vein endothelial cells and human dermal fibroblasts [Ferrao A V, et al., Biochimica et Biophysica Acta (BBA)—Molecular Basis of Disease 1993; 1180(3):225-230; Cariou R, et al., Cell Biology International Reports 1988; 12(12):1037-1047].

Sulfonation, or sulfation, of polymeric materials may induce a biofunction similar to that of heparin [Nguyen T H, et al., Nature Chemistry 2013; 5(3):221-227; Guan R, et al., Bioconjugate Chemistry 2004; 15(1):145-151; Liekens S, et al., Molecular Pharmacology 1999; 56(1):204-213; Sangaj N, et al., Biomacromolecules 2010; 11(12):3294-3300]. However, the nature of these bulk-sized scaffolds may still require invasive surgeries for implantation.

A system that mimics the biofunction of heparin and delivers therapeutic proteins non-invasively to a zone of interest would be an ideal alternative to previous delivery systems. Accordingly, it is an object of the present invention to provide a delivery system for positively charged therapeutic proteins and similar biologically active compounds that overcomes the limitations of prior systems, including the adverse side effects associated with heparin. It is a further object of the invention to provide heparin mimicking delivery system that performs as a reverse thermal gel at physiologically relevant temperatures. As will become apparent in the following disclosure, the present invention meets these important needs.

BRIEF SUMMARY OF THE INVENTION

A unique heparin-mimicking sulfonated reverse thermal gel has been developed. The heparin-mimicking sulfonated reverse thermal gel undergoes typical sol-gel phase transition upon temperature changes and thus achieves a non-invasive treatment. It also acts like heparin for the delivery of therapeutic proteins, while preserving their activity. In addition, the biocompatibility of the sulfonated reverse thermal gel is demonstrated along with its potential as a delivery matrix for positively charged proteins.

In a first aspect the present invention provides a reverse thermal gel composition comprising a graft copolymer, or a pharmaceutically acceptable salt thereof. The graft copolymer will have a main polymer chain, core or backbone (A) and side chains, graft polymers or branches (B). The core (A) can be composed of poly(serinol hexamethylene urea) (PHSU)—also referred to herein as poly[hexamethylene-alt-(serinol; urea)], polyurethane, poly(ester urethane), polyurethaneurea, polyamide, polycarbonate, polyurea, polyacrylate, polyester, polystyrene or polyvinyl compounds and the core polymers comprise one or more sulfonate groups. The graft polymer (B) can be poly(N-isopropylacrylamide) (PNIPAAm), hydroxypropylcellulose, poly(vinylcaprolactame), polyvinyl methyl ether, polyethylene oxide, polyvinylmethylether, polyhydroxyethylmethacrylate, poly(N-acryloylglycinamide), ureido-functionalized polymer, acrylamide-based copolymer, or acrylonitrile-based copolymer compounds. In an advantageous embodiment composition is a gel at 35° C.-40° C. and becomes a liquid at a temperature below this range (e.g. 33° C., 32° C., 31° C., 30° C., 29° C., 28° C., 25° C., 23° C., 20° C., 18° C., or 15° C.).

In a second aspect the present invention provides a method for the parenteral delivery of a liquid sustained release drug to a warm-blooded subject with the resultant formation of a gel depot. The method includes the steps of providing an injectable aqueous solution having uniformly contained therein between about 3 and 40% by weight of a sulfonated graft copolymeric drug delivery liquid and injecting the injectable aqueous solution parenterally into the warm blooded subject. The injectable aqueous solution has an effective amount of a drug dispersed in the sulfonated graft copolymer and the sulfonated graft copolymer has reverse thermal gelation properties with a LCST below the body temperature of the warm blooded animal. The injectable aqueous solution is maintained at a temperature below the LCST of the sulfonated graft copolymer immediately prior to and/or during injection. Keeping the solution below the LCST ensures that it remains in liquid form, which facilitates its injection into the subject. A gel depot of the drug and sulfonated copolymer forms after injection as the temperature of the liquid is raised by the body temperature of the subject above the LCST of the sulfonated graft copolymer.

In a third aspect the present invention provides a reverse thermal gel composition for the delivery of a biologically active agent comprising sulfonated poly(serinol hexamethylene urea)-co-poly(N-isopropylacylamide).

In a fourth aspect the present invention provides a pharmaceutical composition comprising sulfonated poly(serinol hexamethylene urea)-co-poly(N-isopropylacylamide) in combination with one or more positively charged proteins.

In a fifth aspect the present invention provides a pharmaceutical composition comprising a sulfonated reverse thermal gel composed of a graft copolymer having a lower critical solution temperature (LCST) of about 32° C. or less in combination with a therapeutically effective amount of one or more drugs.

BRIEF DESCRIPTION OF THE DRAWINGS

For a fuller understanding of the invention, reference should be made to the following detailed description, taken in connection with the accompanying drawings, in which:

FIG. 1B—Step 3: conjugation of PNIPAAm—COOH to PSHU, and Step 4: sulfonation of PSHU-NIPAAm using 1,3-propane sultone.

DETAILED DESCRIPTION OF THE PREFERRED EMBODIMENT

Figure 5:
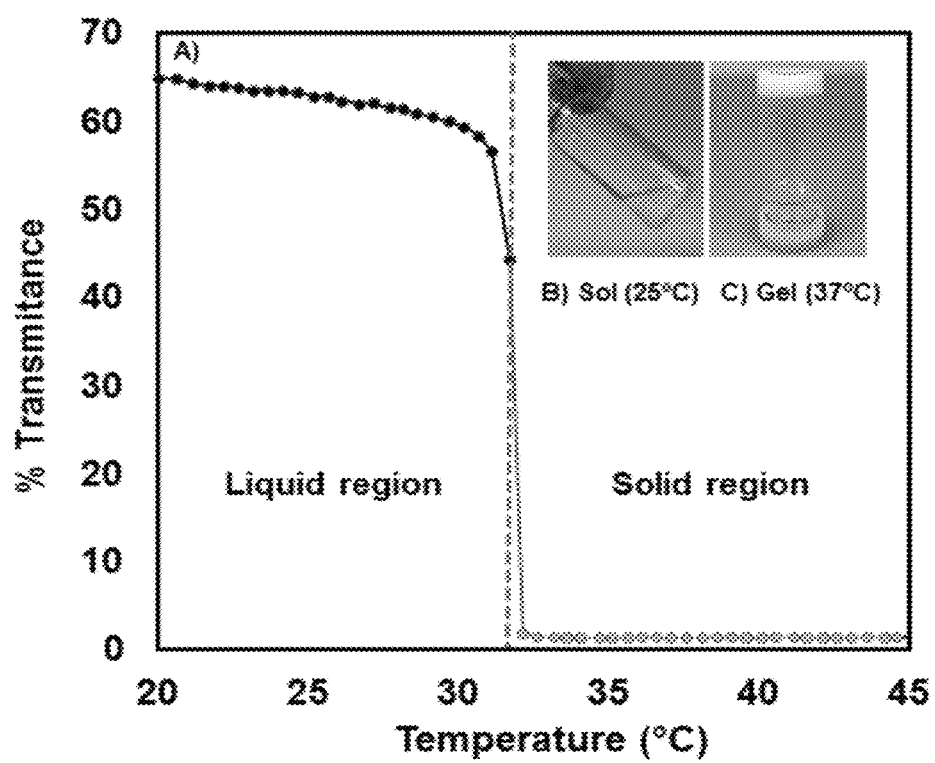
FIG. 5 is a graph (A) with a pair of embedded images (B) & (C) showing temperature-dependent phase transition of sulfonated PSHU-NIPAAm. (A) The sulfonated PSHU-NIPAAm undergoes a sharp, reversible phase transition around 32° C. as determined by UV-Visible spectroscopy. (B) An aqueous solution of sulfonated PSHU-NIPAAm at room temperature (C) turns to physical gel at 37° C.
Figure 9:
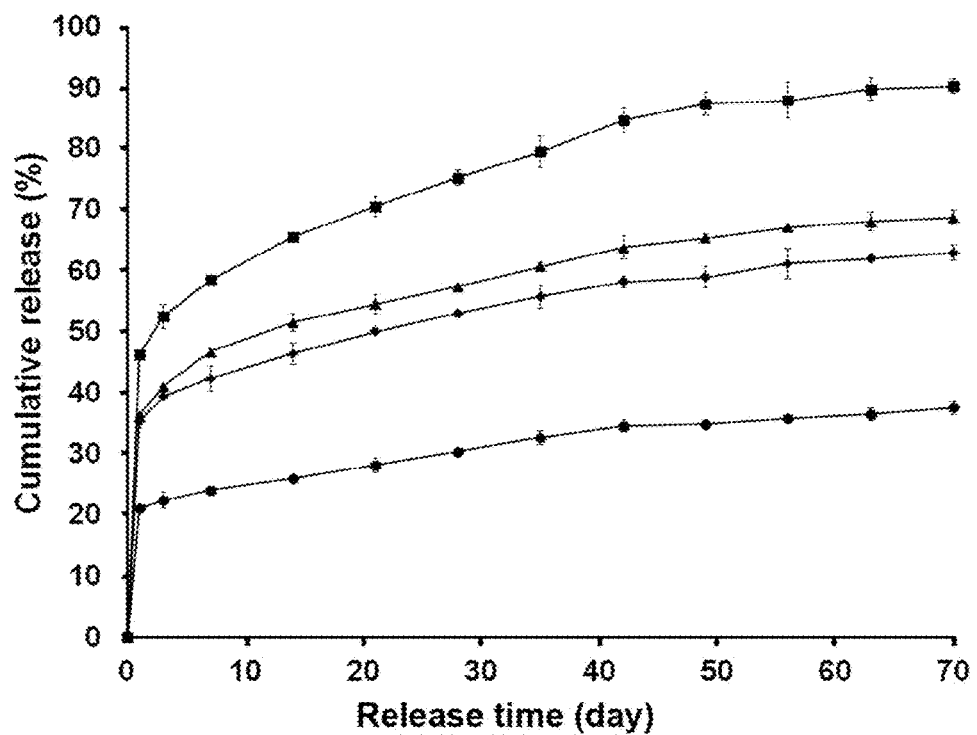
FIG. 9 is a graph showing BSA release profiles from sulfonated PSHU-NIPAAm and plain PSHU-NIPAAm: ♦ sulfonated PSHU-NIPAAm 10%, ● sulfonated PSHU-NIPAAm 15%, ■ plain PSHU-NIPAAm 10%, ▲ plain PSHU-NIPAAm 15%. BSA release was more sustained from sulfonated PSHU-NIPAAm than that from plain PSHU-NIPAAm, with a more sustained profile at higher concentrations. Data represent mean±SD.

Positively charged therapeutic proteins have been used extensively for biomedical applications. However, the safety and efficacy of proteins are mostly limited by their physical and chemical instability and short half-lives in physiological conditions. To this end, we created a heparin-mimicking sulfonated reverse thermal gel (SRTG) as a novel protein delivery system by sulfonation of a graft copolymer, poly (serinol hexamethylene urea)-co-poly(N-isopropylacylamide), or PSHU-NIPAAm. The net charge of the sulfonated PSHU-NIPAAm was negative due to the presence of sulfonate groups. The sulfonated PSHU-NIPAAm showed a typical temperature-dependent sol-gel phase transition, where polymer solutions turned to a physical gel at around 32° C. and maintained gel status at body temperature (FIG. 5). Both in vitro cytotoxicity tests using C2C12 myoblast cells and in vivo cytotoxicity tests by subcutaneous injections demonstrated excellent biocompatibility. In vitro release tests using bovine serum albumin (BSA) revealed that the release from the sulfonated PSHU-NIPAAm was more sustained than that from the plain PSHU-NIPAAm (FIG. 9). Furthermore, this sulfonated PSHU-NIPAAm system did not affect protein structure after 70-day observation periods.

Example 1—Materials and Equipment

Materials

N-Isopropylacrylamide (NIPAAm), anhydrous N,N-dimethylformamide (DMF), 4,4'-azobis(4-cyanovaleric acid) (ACVA), urea, N-BOC-serinol, hexamethylene diisocyanate (HDI), diethyl ether, trifluoroacetic acid (TFA), dichloromethane (DCM), N-(3-dimethylaminopropyl)-N'-ethylcarbodiimide hydrochloride (EDC-HCl), 1,3-propane sultone (PS), bovine serum albumin (BSA), and dimethyl sulfoxide (DMSO) were purchased from Sigma-Aldrich, (St. Louis, Mo., USA). N-Hydroxysuccinimide (NHS) and potassium tert-butoxide (t-BuOK) were purchased from Alfa Aesar (Ward Hill, Mass., USA). 3-(4,5-Dimethylthiazol-2-yl)-2,5-diphenyltetrazolium bromide (MTT) was purchased from Invitrogen Corporation (Carlsbad, Calif., USA). Fetal bovine serum (FBS), penicillin and DME/F-12 1:1 growth medium were purchased from Thermo Scientific (Logan, Utah, USA). Trypsin EDTA IX was purchased from Cellgro (Manassas, Va., USA). C2C12 (ATCC® CRL1772™) cell was purchased from the America Type Culture Collection (Manassas, Va., USA). Monoclonal antibody (host/isotype: IgG1 kappa) for ED-1 staining was purchased from Millipore (Temecula, Calif., USA). Spectra/Por dialysis membranes (MWCO: 3500-5000 and 12,000-14,000 Da) were purchased from Spectrum Laboratories (Rancho Dominguez, Calif., USA).

Equipment

Morphological characterization was carried out by scanning electron microscopy (SEM) using a Field Emission SEM JEOL JSM 7401F. The low critical solution temperature (LCST) was determined using a UV-Visible spectrophotometer with a temperature-controlled cell holder. Molecular weight was determined via gel permeation chromatography (GPC) on an Ecosec GPC system using a TOSOH TSK gel column, anhydrous DMF with 0.1% LiBr as mobile phase, and polystyrene as standard. Proton nuclear magnetic resonance ($^1$H NMR) spectra were recorded on a Bruker Avance 500 NMR. Zeta potential measurements were carried out in a Zetasizer Nano Z (Malvern, Westborough, Mass.) using a DTS1060 cell and analyzed with a zetasizer software. The secondary structure of BSA was determined using a Chirascan-plus circular dichroism (CD) spectrometer (Applied photophysics) at 25° C. and a 1 mm quartz cuvette, by scanning from 200-260 nm with 2 nm increments.

Example 2—Synthesis of SRTG

Synthesis of Poly(Serinol Hexamethylene Urea) or PSHU

N-BOC-serinol (1.147 g, 6 mmol) and urea (0.36 g, 6 mmol) were dissolved in 6 ml of anhydrous DMF in a 25 ml round bottom flask at 90° C. under a nitrogen atmosphere. HDI (2.018 g, 12 mmol) was added slowly, and the polymerization was performed for 7 days. After cooling down to ambient temperature, the mixture was precipitated into excess anhydrous diethyl ether. The precipitate was dissolved again in anhydrous DMF and precipitated into excess anhydrous diethyl ether. The purification process was carried out thrice. Unreacted urea was removed by washing with water, and the polymer was lyophilized at −45° C. for 24 h.

De-Protection of PSHU (PSHU-NH$_2$)

PSHU (1.5 g) was dissolved in 10 ml of a TFA/DCM (1:1, v/v) mixture, and the de-protection was performed for 30 min at room temperature. After removing TFA and DCM using a rotary evaporator, the resulting polymer was re-dissolved in DMF and purified by three precipitations into diethyl ether. Finally, the polymer was decanted in water and lyophilized at −45° C. for 24 h.

Synthesis of PNIPAAm—COOH

NIPAAm (5 g, 800 mmol) and ACVA (0.06 g, 4 mmol) were dissolved in 10 ml of anhydrous DMF in a 25 ml round bottom flask. The solution was purged with pure nitrogen for 30 min. The polymerization was performed for 3 h at 68° C. After cooling down to ambient temperature, the mixture was precipitated into hot water (60° C.). After washing twice in hot water, the polymer was dissolved in milli-Q water and dialyzed (MWCO: 3500-5000 Da) against 1 l water for 24 h at room temperature. The product was lyophilized at −45° C. for 48 h.

Conjugation of PNIPAAm—COOH onto PSHU-NH$_2$ (PSHU-NIPAAm)

PNIPAAm—COOH (0.75 g, 1.21 mmol) was dissolved in 5 ml of anhydrous DMF with three molar excess of EDC-HCl and NHS in a 25 ml round bottom flask at room temperature under a nitrogen atmosphere and the mixture was stirred for 24 h. 1 ml of PSHU-NH$_2$ solution (0.125 g/ml) prepared in anhydrous DMF was added slowly and the reaction was performed for 24 h at room temperature under a nitrogen atmosphere. The mixture was precipitated into excess diethyl ether thrice. The polymer was dissolved in milli-Q water and dialyzed (MWCO: 12,000-14,000 Da) against 1 l water for 24 h at room temperature and the product was lyophilized at −45° C. for 48 h.

Sulfonation of PSHU-NIPAAm

PS (0.034 g, 5 mmol) and t-BuOK (0.032 g, 5 mmol) were dissolved in 3 ml of anhydrous DMF in a 25 ml round bottom flask at 50° C. under a nitrogen atmosphere. A solution of 3 ml PSHU-NIPAAm (0.1 g/ml) in anhydrous DMF was added slowly to the flask and the sulfonation was performed for 3 days at 60° C. under a nitrogen atmosphere. After cooling down to ambient temperature, the mixture was precipitated into excess diethyl ether thrice. Finally, the polymer was dissolved in milli-Q water and dialyzed (MWCO: 12,000-14,000 Da) against 1 l water for 48 h at room temperature and lyophilized at −45° C. for 48 h.

Example 3—Synthesis and Characterization of Sulfonated PSHU-NIPAAm

Figure 1A:
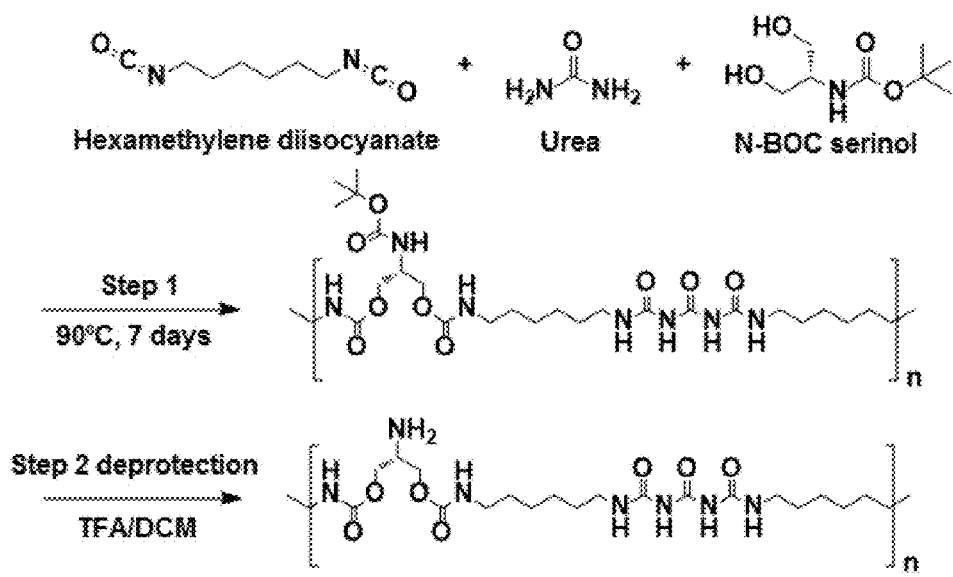
FIG. 1A is a series of diagrams showing the first two steps in the four step synthesis of sulfonated PSHU-NIPAAm—Step 1: synthesis of PSHU, Step 2: de-protection of PSHU.
Figure 1B:
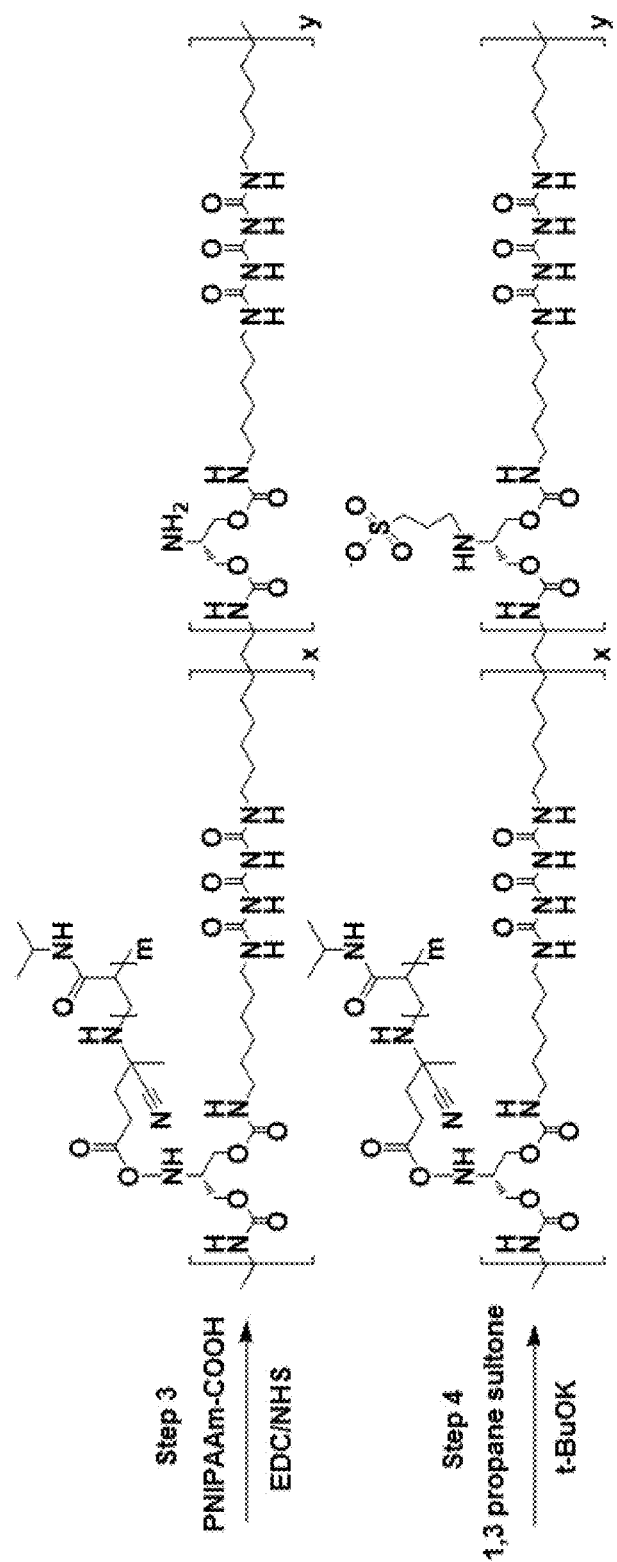
FIG. 1B is a series of diagrams showing the last two steps in the four step synthesis of sulfonated PSHU-NIPAAm.
Figure 2:
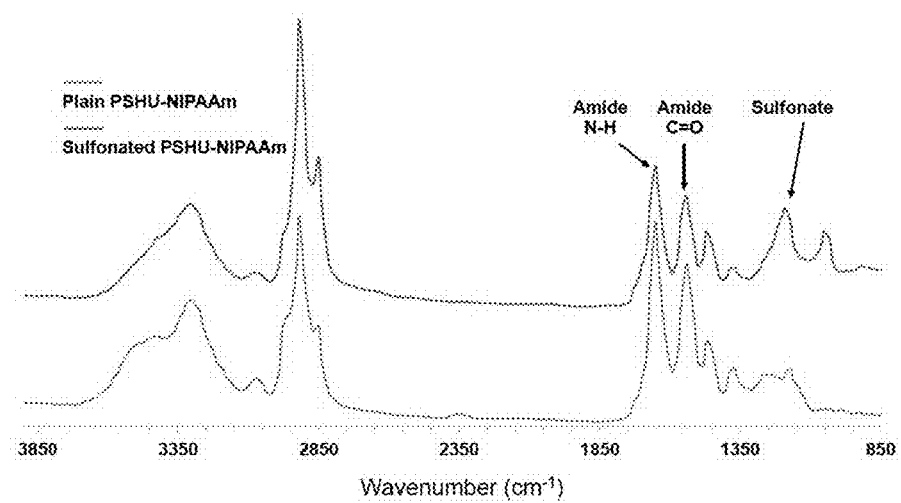
FIG. 2 is a graph showing FTIR spectra of sulfonated PSHU-NIPAAm and plain PSHU-NIPAAm. The signals represent (from right to left) sulfonate groups (995 $cm^{-1}$), amide carbonyl (1500 $cm^{-1}$) and amide amine (1645 $cm^{-1}$). Note that "Plain" is the lower plot, while "Sulfonated" is the upper plot.
Figure 3:
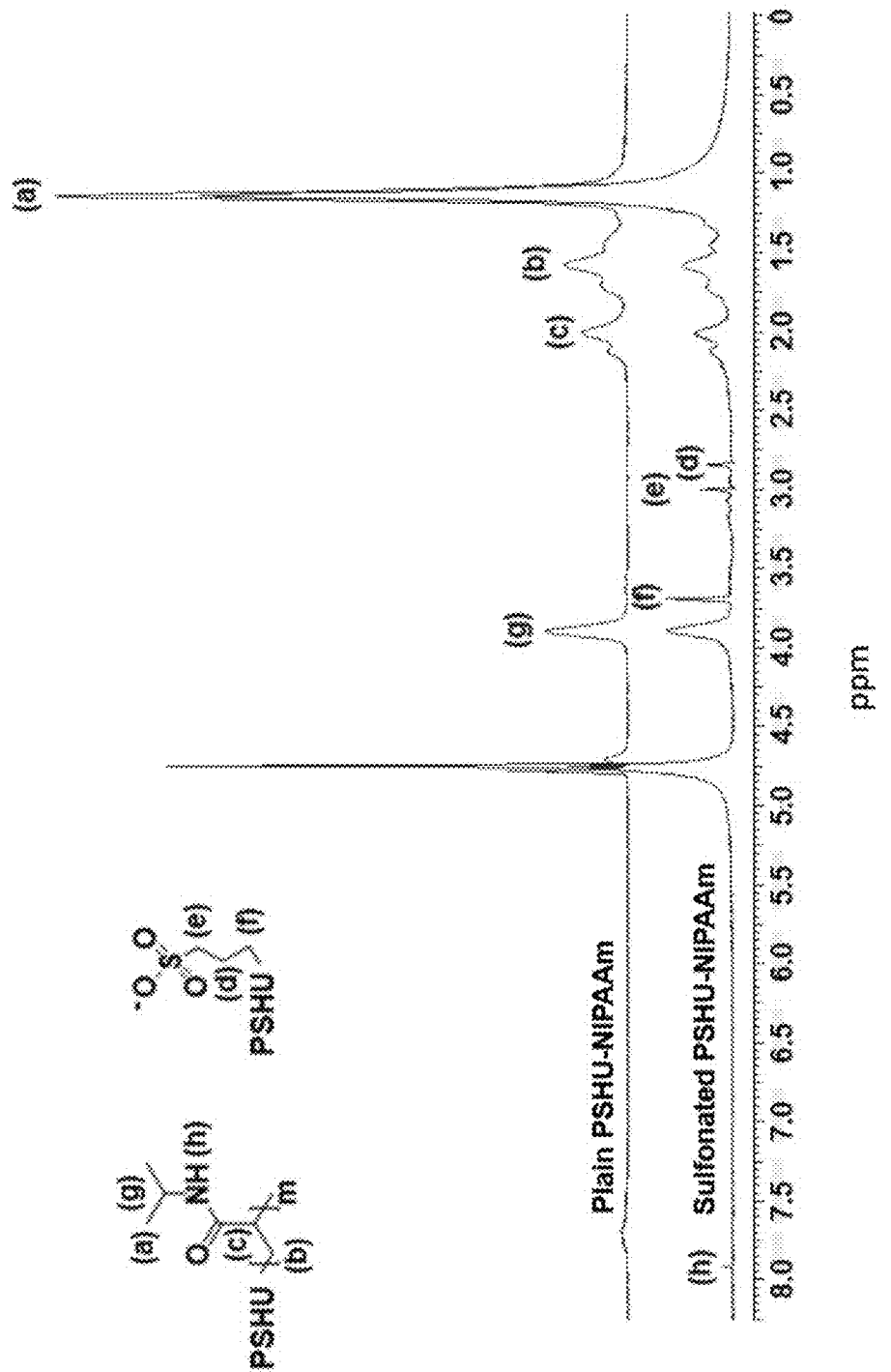
FIG. 3 is a graph showing $^1$H NMR spectra of sulfonated PSHU-NIPAAm and plain PSHU-NIPAAm. Successful sulfonation of PSHU-NIPAAm was confirmed by the presence of a methylene proton adjacent to sulfur ($O_3S$—$CH_2$) at 3.01 ppm. In addition, the conjugation of PNIPAAm was confirmed by the presence of methylene and methyl protons at 1.55 and 1.09 ppm, respectively.

With an aim to create a heparin-mimicking polymer that possesses the biofunction of natural heparin and presents the advantages of an RTG, the sulfonated PSHU-NIPAAm was synthesized using PSHU-NIPAAm copolymer (FIG. 1). While the primary amine in PSHU is initially protected by a BOC group, it is easily de-protected to a primary amine in the mixture of TFA/DCM. These de-protected primary amines can then be used for further modifications. The presence of both sulfonate groups and PNIPAAm in sulfonated PSHU-NIPAAm was confirmed by FTIR (FIG. 2) and $^1$H NMR (FIG. 3). FTIR showed sulfonate (O=S=O) vibrations at 995 cm$^{-1}$, while no signals of sulfonate groups were observed in plain PSHU-NIPAAm (FIG. 2). In both plain PSHU-NIPAAm and sulfonated PSHU-NIPAAm amide amine (N—H) and amide carbonyl (C=O) peaks were observed at 1645 cm$^{-1}$ and 1500 cm$^{-1}$, respectively. The presence of sulfonate group was further confirmed by $^1$H NMR (FIG. 3). The methylene proton adjacent to sulfur ($^-$O$_3$S—CH$_2$) was confirmed at 3.01 ppm [Weaver J V M, et al., Chemical Communications 2002(18):2122-2123] that does not exist in plain PSHU-NIPAAM. In addition, the presence of methylene and methyl protons at 1.55 and 1.09 ppm, respectively, also confirmed PNIPAAm in the polymer.

GPC was used to investigate the molecular weight ($M_w$) of sulfonated PSHU-NIPAAm and plain PSHU-NIPAAm, which were found to be 100,129 Da and 77,302 Da, respectively, corroborating the further functionalization of amine groups.

Figure 4:
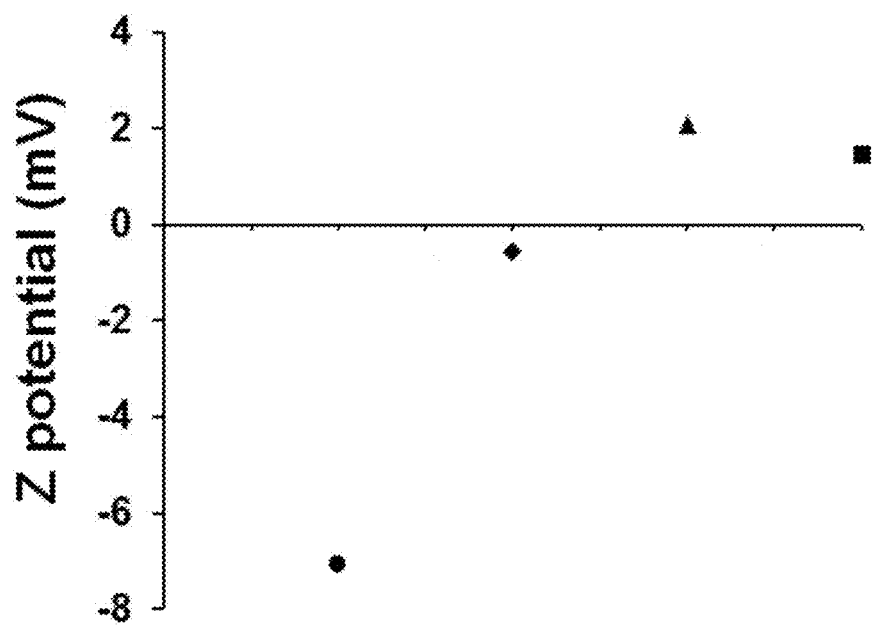
FIG. 4 is a graph showing the zeta potential of sulfonated PSHU-NIPAAm and plain PSHU-NIPAAm. The plain PSHU-NIPAAm showed positive zeta potential: 1.47 mV for 10% (■) and 2.08 mV for 15% (▲). In contrast, the zeta potential of sulfonated PSHU-NIPAAm showed negative values due to the negatively charged sulfonate groups: −0.56 mV for 10% (♦) and −7.05 mV for 15% (●).

The introduction of sulfonate groups onto PSHU-NIPAAm may lead to a shift in the net charge to more negative state [Chu H H, et al., Journal of Controlled Release 2011; 150(2):157-163]. The charge shifts before and after the sulfonation were verified by zeta potential analysis (FIG. 4). The zeta potential of 10% and 15% (wt/v) plain PSHU-NIPAAm were 1.47 and 2.08, respectively, while sulfonated PSHU-NIPAAm showed negative values due to the presence of negatively charged sulfonate groups. In addition, a higher concentration of sulfonated PSHU-NIPAAm resulted in higher negative charges (−0.56 mV and −7.05 mV for 10% and 15%, respectively), indicating that the negative charge intensity can be easily modulated by simple variations of polymer concentrations.

The sol-gel phase transition of sulfonated PSHU-NIPAAm was determined by estimating its low critical solution temperature (LCST) (FIG. 5). The transmittance of an aqueous solution of sulfonated PSHU-NIPAAm decreased slowly upon heating from 20° C. to 31° C., reached almost zero at 32° C., and turned to an opaque solid upon further heating over 33° C., indicating that the aqueous solution turns to a physical gel as the temperature increases. This phase transition is driven purely by the thermodynamic competition between hydration of the polymer chains and hydrophobic interactions between polymer molecules [Park D, et al., Biomaterials 2011; 32(3):777-786]. At low temperatures (below the LCST, 32° C. in this case), hydration is thermodynamically favored and the polymer molecules are maintained in a solution state (FIG. 5B). Above the LCST, hydrophobic interactions between the polymer chains are favored and the polymer molecules interact to form a self-standing physical gel (FIG. 5C).

Figure 6:
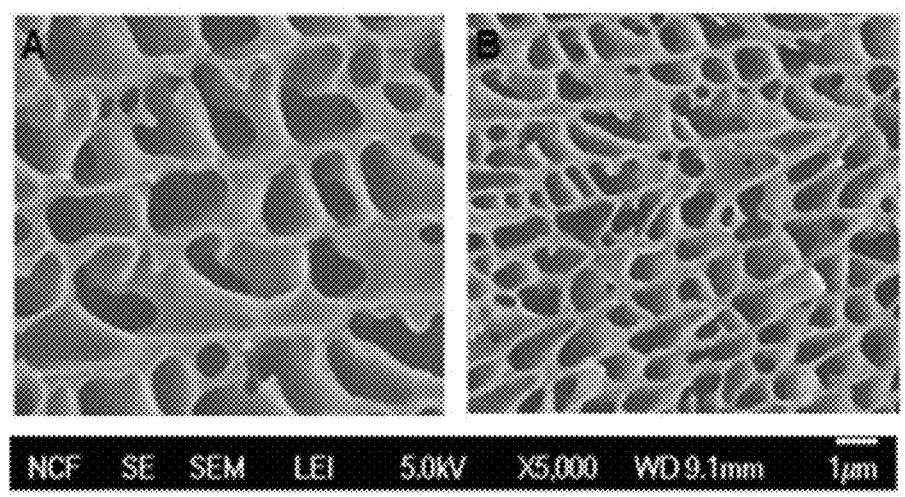
FIG. 6 is a pair of images showing SEM images of sulfonated PSHU-NIPAAm cross-section. (A) 10% (w/v) and (B) 15% (w/v) of sulfonated reverse thermal gel (SRTG), with larger pore size in the lower concentration of sulfonated PSHU-NIPAAm.

The morphological characterization of 10% and 15% (wt/v) sulfonated PSHU-NIPAAm was achieved by SEM (FIG. 6). Cross-sectional images of the gels revealed that both concentrations resulted in a highly porous configuration. It is also noticeable that a higher concentration of the polymer solution formed smaller pores than the lower concentration (0.48±0.1 μm and 1.11±0.3 μm for 15% and 10%, respectively), indicating that the pore size of sulfonated PSHU-NIPAAm could be easily tuned by polymer concentrations, which may be beneficial for modulating protein release from the matrix.

Example 4—Cytotoxicity Testing

Cytotoxicity Testing Protocol:

In vitro cytotoxicity testing was performed by MTT assay using C2C12 myoblast cells by ISO 10993-5 guidelines. Briefly, C2C12 cells were seeded into 96-well plate (10,000 cells/well) and incubated with 100 μL of sequentially diluted polymer extract at 37° C. for 24 h. The cell viability was examined by MTT assay.

In vivo cytotoxicity test was performed by subcutaneous injection into male Sprague-Dawley rats (~230 g). All animal experiments were performed under a protocol approved by the Institutional Animal Care and Use Committees (IACUC) at the University of Colorado Denver. The rats were anesthetized by isoflurane inhalation. Rats were injected subcutaneously with 0.5 ml of SRTG solution on the right and left side of their back. The animals were sacrificed 1, 7, and 10 days post-injection; tissues were fixed in 10% formalin and cryo-sectioned longitudinally to 8 μm thickness. The sectioned tissues were fixed in acetone for 10 min, air dried, and incubated in mouse anti-rat ED1 primary antibody for 30 min at 37° C. After washing with PBS three times, the tissues were incubated in goat anti-mouse Cy3 secondary antibody for 30 min at room temperature. ED1-positive cells in square millimeters were imaged and quantified.

Figure 7:
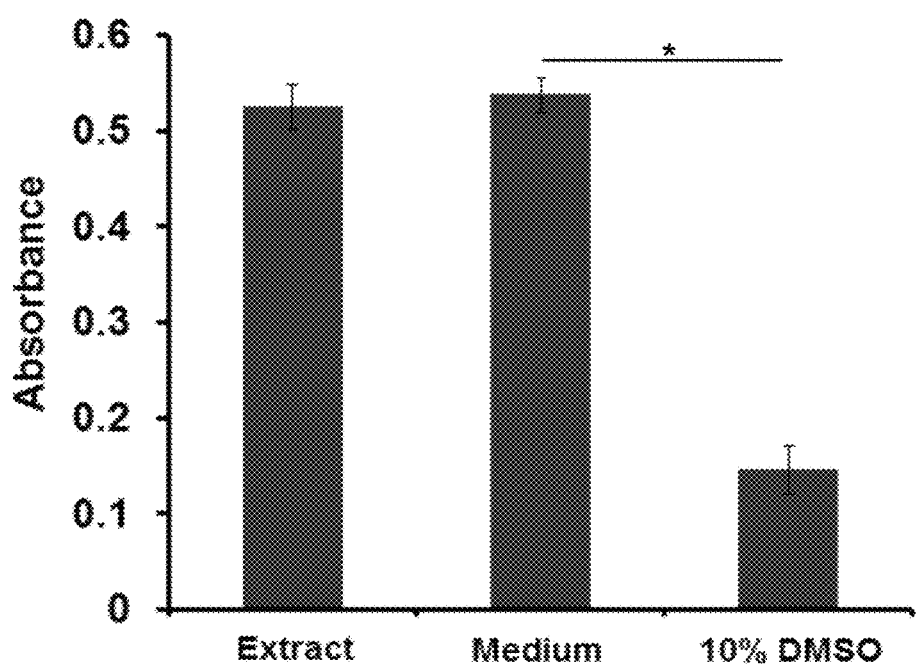
FIG. 7 is a graph showing the in vitro cytotoxicity of sulfonated PSHU-NIPAAm by MTT assay. Results demonstrated no cytotoxic effects of sulfonated PSHU-NIPAAm on C2C12 cells after exposure to the polymer extract in medium, while 10% DMSO shows significant cytotoxicity. There is no statistical difference between medium and polymer extracts. Data represent mean±SD. * indicates p value <0.05 (Student's test).

Cytotoxicity Testing:

In vitro cytotoxicity was investigated using an MTT assay with C2C12 myoblast cells, a well-documented method for measuring cell viability and providing a general indication of cell health [Supino R. MTT assays. *Methods Mol. Biol* 1995; 43:137-149; Meerloo J, et al., Cell Sensitivity Assays: The MTT Assay. *Methods Mol. Biol.* 2011; 731:237-245; Moradhaseli S, et al., *Iran. J. Pharm. Res.* 2013; 12:155-163]. FIG. 7 shows no statistical difference between the absorbance (directly related to cellular metabolic activity) of pure medium (positive control) and the polymer extract, while the presence of 10% DMSO significantly reduced the level of absorbance. The similar absorbance levels of the extract and the medium is good evidence that the sulfonated PSHU-NIPAAm is non-cytotoxic. In this study, we did not include plain PSHU-NIPAAm as a control group, since in our previous study plain PSHU-NIPAAm proved to have good biocompatibility [Yun. D, et al., Austin Journal of Biomedical Engineering 2014; 1(4). http://austinpublishinggroup.org/biomedical-engineering/onlinefirst.php].

Figure 8:
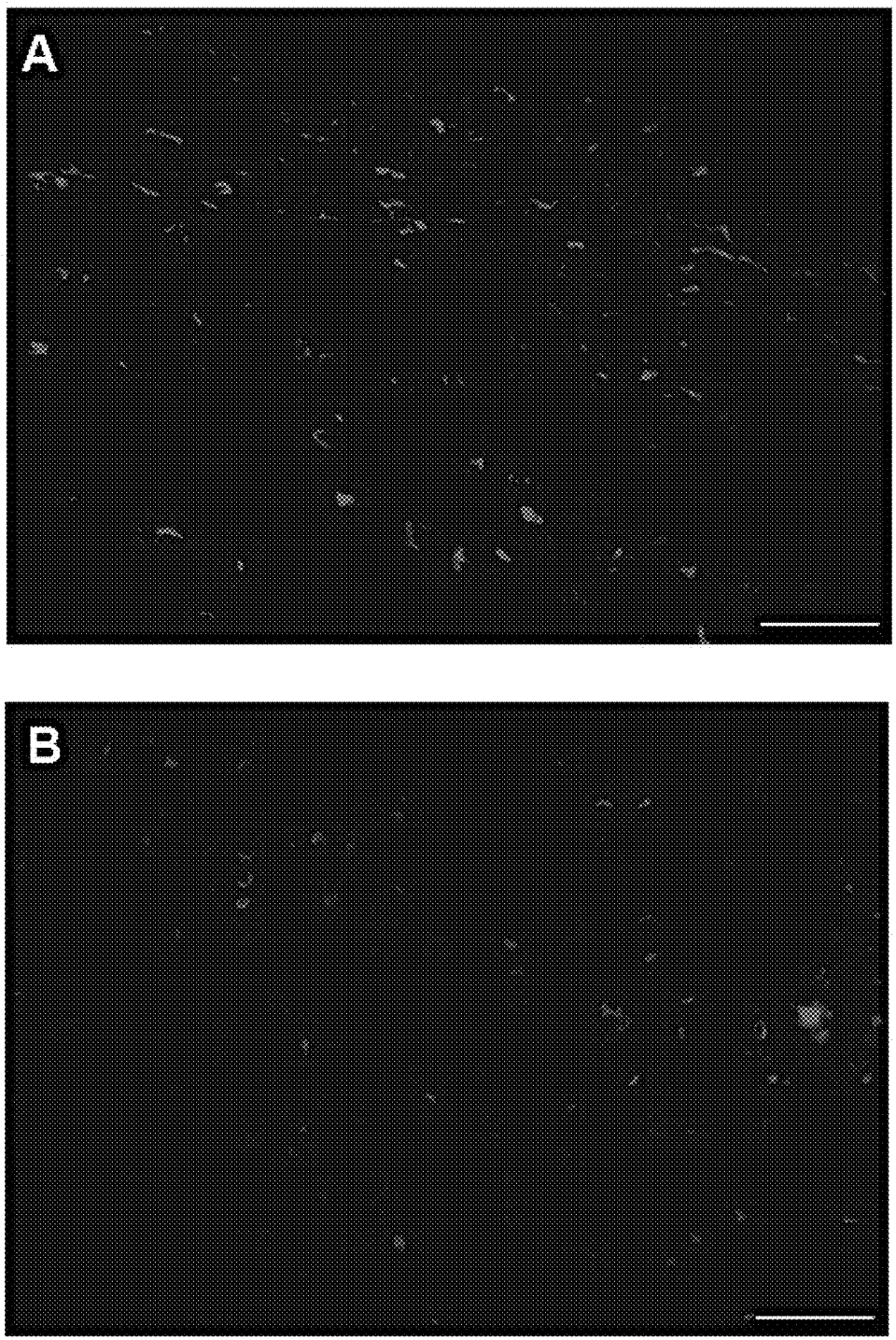
FIG. 8 is a series of three (3) images, labeled (A)-(C), and a graph, labeled (D), showing immunohistochemically stained ED1-positive macrophages (200×, scale bar=70 μm). Tissues were harvested after (A) 1 day, (B) 7 days, and (C) 10 days. (D) The decrease in the number of ED1-positive macrophages with time indicates a reduction in the inflammatory response. Data represent mean±SD.

In vivo cytotoxicity was further investigated by subcutaneous injection of sulfonated PSHU-NIPAAm solution into male Sprague-Dawley rats (~230 g). We injected 27% (wt/v, the highest possible concentration in water) sulfonated PSHU-NIPAAm solution using a 25-gauge needle. The inflammatory reaction was examined using ED1 staining to estimate the macrophage activity triggered by injection of the gel (FIG. 8). At day-1 (FIG. 8A), a large number of ED1-positive macrophages were found, indicating an acute inflammatory reaction caused by a non-specific inflammatory reaction [Sundback C A, et al., Biomaterials 2005; 26(27):5454-5464]. The density of ED1-positive cells decreased rapidly after 7 days (FIG. 8B), and most of the ED1-positive cells disappeared after 10 days (FIG. 8C) indicating a mild inflammatory reaction. ED1-positive macrophages were quantified using 10 randomly chosen images around the tissue-gel interface. The sequential decrease in the number of macrophages was observed (FIG. 8D), indicating excellent biocompatibility even at the highest dose.

Example 5—BSA Release Testing

BSA Release Test Protocol:

Two concentrations (10% and 15%, w/v) of the sulfonated PSHU-NIPAAm-BSA solution were prepared in pH 4.5 acetate buffer solution with a final BSA concentration of 0.5 mg/ml. The mixtures were stirred for 30 min at 4° C. A 300 μl of the sulfonated PSHU-NIPAAm-BSA solution was poured into a cylindrical mold, and allowed to form a disc-shaped gel at 37° C. Once the disc-shaped gel was formed, it was transferred into a vial containing 10 ml of pH 4.5 acetate buffer solution and incubated at 37° C. At pre-determined time points, 3 ml of sample was withdrawn, and the released BSA concentration was quantified by UV-Vis spectrometer at 280 nm and expressed as cumulative percent release. The same experiment was performed with the plain PSHU-NIPAAm for the comparison.

BSA Release Testing:

The potential of sulfonated PSHU-NIPAAm as a protein delivery system was studied using BSA with different concentrations of sulfonated PSHU-NIPAAm and plain PSHU-NIPAAm (FIG. 9). The sulfonated PSHU-NIPAAm showed remarkably more sustained release behavior than plain PSHU-NIPAAm, indicating that the negatively charged sulfonate groups in the sulfonated PSHU-NIPAAm may effectively hold BSA in the matrix (Note that BSA shows positive charge at pH 4.5). Moreover, the fact that BSA release was more sustained at higher concentrations well supports that the release rate can be easily modulated by changing the sulfonated PSHU-NIPAAm concentration. A possible explanation is that higher concentrations of the sulfonated PSHU-NIPAAm leads to a higher sulfonate group density in a given volume of the gel matrix, resulting in more negative charge (as confirmed by zeta potential measurement in FIG. 4), which causes enhanced ionic interaction between sulfonated PSHU-NIPAAm and BSA. Thus, the sulfonated PSHU-NIPAAm system is a valuable tool for controlled and sustained protein delivery.

Example 6—Circular Dichroism (CD) Spectroscopy

Figure 10:
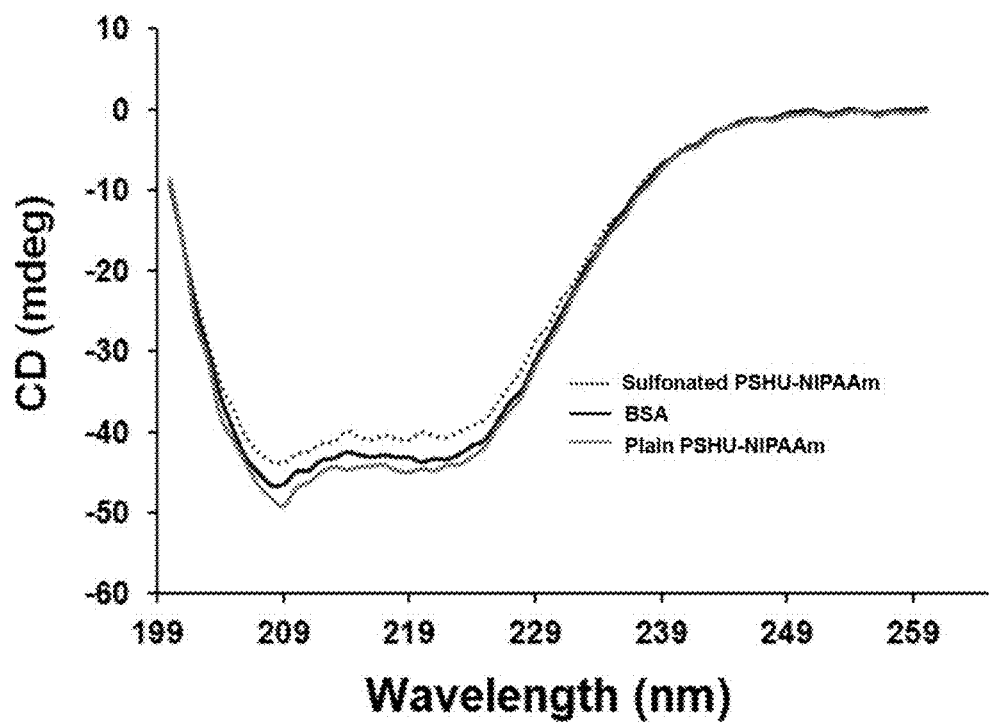
FIG. 10 is a graph showing the circular dichroism spectra (CD) of native and released BSA. The similarity of the protein conformation between samples indicates that the secondary structure of the BSA protein was well preserved by the system.

In order for the sulfonated PSHU-NIPAAm to serve as a protein delivery matrix, it should not affect protein structure or possibly lead to the denaturation of proteins. To address these issues and confirm that proteins maintain their structure, the secondary structure of released BSA at the last day of observation was determined by CD spectroscopy and compared with native BSA solution (FIG. 10). No significant difference was observed in all samples with a typical α-helix conformation [Greenfield N J. Nature Protocols 2006:1(6):2876-2890, Nelson D M, et al., Journal of Biomedical Materials Research Part A 2012; 100A(3):776-785; Xiao Q, et al., Journal of Photochemistry and Photobiology A: Chemistry 2012; 249(0):53-60], confirming well-preserved protein structure.

A novel heparin-mimicking injectable sulfonated PSHU-NIPAAm was successfully synthesized, demonstrating typical sol-gel phase transition upon temperature changes and remarkably sustained BSA release profile compared to a plain PSHU-NIPAAm with capacity to preserve protein structure. This sulfonated PSHU-NIPAAm system can serve as a platform for biomimetic injectable biomaterials for controlled and sustained protein delivery in biomedical applications.

GLOSSARY OF CLAIM TERMS

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, the term "patient" or "subject" refers to members of the animal kingdom including but not limited to human beings.

The term "administration" and variants thereof (e.g., "administering" a compound) in reference to a compound of the invention means introducing the compound into the system of the subject in need of treatment. When a compound of the invention is provided in combination with one or more other active agents (e.g., a cytotoxic agent, etc.), "administration" and its variants are each understood to include concurrent and sequential introduction of the compound and other agents.

Kits for practicing the methods of the invention are further provided. By "kit" is intended any manufacture (e.g., a package or a container) comprising at least one reagent, e.g., a pH buffer of the invention. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

In an advantageous embodiment, the kit containers may further include a pharmaceutically acceptable carrier. The kit may further include a sterile diluent, which is preferably stored in a separate additional container. In another embodiment, the kit further comprising a package insert comprising printed instructions directing the use of a combined treatment of an pH buffer and the agent. The kit may also comprise additional containers comprising additional anticancer agents, agents that enhances the effect of such agents, or other compounds that improve the efficacy or tolerability of the treatment.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

"Parenteral" shall mean any route of administration other than the alimentary canal and shall specifically include intramuscular, intraperitoneal, intra-abdominal, subcutaneous, and, to the extent feasible, intravenous.

"Solution", "aqueous solution" and the like, when used in reference to a combination of drug and biodegradable graft copolymer contained in such solution, shall mean a water-based solution having such drug/polymer combination dissolved or uniformly suspended therein at a functional concentration and maintained at a temperature below the LCST of the graft copolymer.

"Drug delivery liquid" or "drug delivery liquid having reverse thermal gelation properties" shall mean a "solution" suitable for injection into a warm-blooded animal which forms a depot upon having the temperature raised above the LCST of the copolymer.

"Depot" means a drug delivery liquid following injection into a warm-blooded animal which has formed a gel upon the temperature being raised to or above the LCST.

"LCST, or lower critical solution temperature", means the temperature at which the biodegradable graft copolymer undergoes reverse thermal gelation, i.e. the temperature below which the copolymer is soluble in water and above which the block copolymer undergoes phase separation to form a semi-solid containing the drug and the block copolymer.

The terms "LCST", "gelation temperature" and "reverse thermal gelation temperature" or the like shall be used interchangeably in referring to the LCST.

"Gel", when used in reference to a semi-solid combination of drug and graft copolymer at a temperature at or above the LCST, shall be inclusive of such combinations in the form of gels, emulsions, dispersions, suspensions and the like.

"Biodegradable" means that the graft polymer can break down or degrade within the body to non-toxic components after all drug has been released.

"Drug" shall mean any organic compound or substance having bioactivity and adapted or used for a therapeutic purpose.

"Peptide", "polypeptide", "oligopeptide" and "protein" shall be used interchangeably when referring to peptide or protein drugs and shall not be limited as to any particular molecular weight, peptide sequence or length, field of bioactivity or therapeutic use unless specifically stated.

As used herein, the term "polymer composition" is a composition comprising one or more polymers. As a class, "polymers" includes homopolymers, heteropolymers, co-polymers, block polymers, block co-polymers and can be both natural and synthetic. Homopolymers contain one type of building block, or monomer, whereas co-polymers contain more than one type of monomer. The polymers described herein are said to be bioerodible or biodegradable.

By that, it is meant that the polymer, once implanted and placed in contact with bodily fluids and tissues, or subjected to other environmental conditions, such as composting, will degrade either partially or completely through chemical reactions, typically and often preferably over a time period of hours, days, weeks or months.

Graft copolymers are polymers composed of a main polymer chain, or backbone, to which one or more side chains, or branches, are chemically connected through covalent bonds.

Provided is a reverse thermal gel composition. The composition is in solution at a lower temperature, e.g., at room temperature and transitions to a gel as the temperature is raised, to form a complete gel at a higher temperature, e.g., physiological (body) temperature (e.g., 35° C.-40° C.). The transition temperature also may be referred to as the Lower Critical Solution Temperature, or LCST) is preferably 32° C. or less or 25° C.-32° C. (e.g. 25° C., 26° C., 27° C., 28° C., 29° C., 30° C. 31° C. or 32° C.). As an example, the transition point is above room temperature (RT, for example 25° C.) and below physiological temperature (typically 37° C. but there can be individual differences). As a further example, the composition begins transformation as the temperature rises from 25° C. and forms a gel around 33-35° C. (e.g. 33° C., 34° C., or 35° C.) and still remains gel at 37° C.

The polymer compositions may be modified to include biologically active groups or active agents either covalently bound (attached) to the polymer structure or bound to the structure non-covalently. Active agents can be admixed with the polymer composition, absorbed or adsorbed into the composition. Active agents that may be incorporated into the compositions described herein include, without limitation, anti-inflammatories, such as, without limitation, NSAIDs (non-steroidal anti-inflammatory drugs) such as salicylic acid, indomethacin, sodium indomethacin trihydrate, salicylamide, naproxen, colchicine, fenoprofen, sulindac, diflunisal, diclofenac, indoprofen sodium salicylamide, antiinflammatory cytokines, and antiinflammatory proteins or steroidal antiinflammatory agents; antibiotics; anticlotting factors such as heparin, Pebac, enoxaprin, aspirin, hirudin, plavix, bivalirudin, prasugrel, idraparinux, warfarin, Coumadin, clopidogrel, PPACK, GGACK, tissue plasminogen activator, urokinase, and streptokinase; growth factors. Other active agents include, without limitation: (1) immunosuppressants, glucocorticoids such as hydrocortisone, betamethasone, dexamethasone, flumethasone, isoflupredone, methylpred-nisolone, prednisone, prednisolone, and triamcinolone acetonide; (2) antiangiogenics such as fluorouracil, paclitaxel, doxorubicin, cisplatin, methotrexate, cyclophosphamide, etoposide, pegaptanib, lucentis, tryptophanyl-tRNA synthetase, retaane, CA4P, AdPEDF, VEGF-TRAP-EYE, AG-103958, Avastin, JSM6427, TG100801, ATG3, OT-551, endostatin, thalidomide, becacizumab, neovastat; (3) antiproliferatives such as sirolimus, paclitaxel, perillyi alcohol, farnesyl transferase inhibitors, FPTIII, L744, antiproliferative factor, Van 10/4, doxorubicin, 5-FU, Daunomycin, Mitomycin, dexamethasone, azathioprine, chlorambucil, cyclophosphamide, methotrexate, mofetil, vasoactive intestinal polypeptide, and PACAP; (4) antibodies; drugs acting on immunophilins, such as cyclosporine, zotarolimus, everolimus, tacrolimus and sirolimus (rapamycin), interferons, TNF binding proteins; (5) taxanes, such as paclitaxel and docetaxel; statins, such as atorvastatin, lovastatin, simvastatin, pravastatin, fluvastatin and rosuvastatin; (6) nitric oxide donors or precursors, such as, without limitation, Angeli's Salt, L-Arginine, Free Base, Diethylamine NONOate, Diethylamine NONOate/AM, Glyco-SNAP-1, Glyco-SNAP-2, (.+−.)-S-Nitroso-N-acetylpenicillamine, S-Nitrosoglutathione, NOC-5, NOC-7, NOC-9, NOC-12, NOC-18, NOR-1, NOR-3, SIN-1, Hydrochloride, Sodium Nitroprusside, Dihydrate, Spermine NONOate, Streptozotocin; and (7) antibiotics, such as, without limitation: acyclovir, afloxacin, ampicillin, amphotericin B, atovaquone, azithromycin, ciprofloxacin, clarithromycin, clindamycin, clofazimine, dapsone, diclazaril, doxycycline, erythromycin, ethambutol, fluconazole, fluoroquinolones, foscarnet, ganciclovir, gentamicin, iatroconazole, isoniazid, ketoconazole, levofloxacin, lincomycin, miconazole, neomycin, norfloxacin, ofloxacin, paromomycin, penicillin, pentamidine, polymixin B, pyrazinamide, pyrimethamine, rifabutin, rifampin, sparfloxacin, streptomycin, sulfadiazine, tetracycline, tobramycin, trifluorouridine, trimethoprim sulphate, Zn-pyrithione, and silver salts such as chloride, bromide, iodide and periodate.

Pharmaceutically acceptable salts are, because their solubility in water is greater than that of the initial or basic compounds, particularly suitable for medical applications. These salts have a pharmaceutically acceptable anion or cation. Suitable pharmaceutically acceptable acid addition salts of the compounds of the invention include, without limitation, salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts include without limitation, ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine. Pharmaceutically acceptable salts may be prepared from parent compounds by any useful method, as are well known in the chemistry and pharmaceutical arts.

In one embodiment of the methods described herein, the composition is injected or deposited at the site targeted for treatment. For instance a catheter, cannula, trochar, syringe, etc. can be used to deliver the composition to a desired location.

The compositions described herein are useful for drug delivery, especially were systemic treatment is not necessary or is dangerous. One or more therapeutic agents may be included in the compositions and the composition is delivered to a site in a patient, where the composition gels. Delivery of the composition is limited by the rate of degradation of the polymeric component of the composition. As such, the composition may be useful in treating tumors, for example, by complexing an anticancer agent with the polymeric component of the composition and delivering the composition to the site of a tumor, where it slowly releases the anticancer agent. Likewise, these compositions may find use in treating localized conditions, such as abscesses. The composition may be useful in delivering steroids at a constant rate, for example in the case of testosterone, where less than optimal injections, topical gels and patches are the norm, or contraceptives.

In any use for the prevention and/or treatment of any condition in a patient, a person of ordinary skill in the pharmaceutical and medical arts will appreciate that it will be a matter of simple design choice and optimization to identify a suitable dosage regimen for treatment of any given condition using the delivery systems/compositions described herein. As such, the composition may comprise a carrier, which comprises acceptable excipients, such as, without limitation, one or more suitable: vehicle(s), solvent(s), diluent(s), pH modifier(s), buffer(s), salt(s), colorant(s), rheology modifier(s), lubricant(s), antifoaming agent(s), hydrogel(s), surfactant(s), emulsifier(s), adjuvant(s), preservative(s), phospholipid(s), fatty acid(s), mono-, di- and tri-glyceride(s) and derivatives thereof, wax (es), oil(s) and water, as are broadly known in the pharmaceutical arts.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A reverse thermal gel composition comprising a sulfonated graft copolymer wherein the composition is a gel at 35° C.-40° C. and a liquid solution at a lower temperature.

2. The reverse thermal gel composition according to claim 1 wherein the sulfonated reverse thermal gel is sulfonated poly(serinol hexamethylene urea)-co-poly(N-isopropylacylamide).

3. The reverse thermal gel composition according to claim 1 wherein the graft copolymer comprises a poly(serinol hexamethylene urea) (PHSU) backbone.

4. The reverse thermal gel composition according to claim 1 wherein the graft copolymer comprises a poly(N-isopropylacrylamide) (PNIPAAm) side chain.

5. The reverse thermal gel composition according to claim 1 wherein the lower critical solution temperature (LCST) of about 32° C. or less.

6. The reverse thermal gel composition according to claim 1 further comprising one or more polypeptides suspended within the sulfonated graft copolymer.

7. The reverse thermal gel composition according to claim 6 wherein the polypeptide is bound to the sulfonate moiety of the sulfonated graft copolymer.

8. The reverse thermal gel composition according to claim 6 wherein the polypeptide is a growth factor.

9. The reverse thermal gel composition according to claim 6 wherein the sulfonated graft copolymer is an injectable solution that forms biodegradable polymeric matrix into which the protein has been incorporated upon gelation and the polymeric matrix provides for the sustained release of the polypeptide following injection and gelation within a subject.

10. An aqueous solution of the reverse thermal gel composition according to claim 1 wherein the sulfonated graft copolymer comprises between about 3 and 40% weight-to-volume of the aqueous solution.

11. The aqueous solution of the reverse thermal gel composition according to claim 10 wherein the sulfonated graft copolymer concentration is adjusted to vary the pore size of the resulting polymeric matrix or the charge density.

12. The aqueous solution of the reverse thermal gel composition according to claim 1 wherein the sulfonated graft copolymer comprises between about 10 and 15% weight-to-volume of the aqueous solution.

13. A reverse thermal gel composition comprising:
   a sulfonated graft copolymer that is a gel or solid at a physiologic or pathologic temperature and a liquid or sol at room temperature; and
   a growth factor.

14. The reverse thermal gel composition according to claim 13 wherein the sulfonated graft copolymer is an injectable solution that forms biodegradable polymeric matrix into which the growth factor has been incorporated upon gelation and the polymeric matrix provides for the sustained release of the growth factor following injection and gelation within a subject.

15. A reverse thermal gel composition comprising:
   a sulfonated graft copolymer that is a gel or solid at a physiologic or pathologic temperature and a liquid at room temperature; and
   a polypeptide.

16. The reverse thermal gel composition according to claim 15 wherein the sulfonated graft copolymer is an injectable solution that forms biodegradable polymeric matrix into which the protein has been incorporated upon gelation and the polymeric matrix provides for the sustained release of the protein following injection and gelation within a subject.

17. The reverse thermal gel composition according to claim 15 wherein the sulfonated reverse thermal gel is sulfonated poly(serinol hexamethylene urea)-co-poly(N-isopropylacylamide).

18. The reverse thermal gel composition according to claim 15 wherein the graft copolymer comprises a poly(serinol hexamethylene urea (PHSU) backbone.

19. The reverse thermal gel composition according to claim 15 wherein the graft copolymer comprises a poly(N-isopropylacrylamide) (PNIPAAm) side chain.

20. The reverse thermal gel composition according to claim 15 wherein the physiologic or pathologic temperature is the temperature of a warm-blooded subject.

* * * * *